United States Patent
Gonzalez Penas et al.

(10) Patent No.: US 11,453,853 B2
(45) Date of Patent: Sep. 27, 2022

(54) METHOD FOR CLEANING A SOLID SUPPORT OF A FERMENTATION REACTOR COMPRISING A CONTAMINATED POLYURETHANE FOAM

(71) Applicant: IFP Energies Nouvelles, Rueil-Malmaison (FR)

(72) Inventors: Helena Gonzalez Penas, Rueil-Malmaison (FR); Marcel Ropars, Palaiseau (FR); Eszter Toth, Rueil-Malmaison (FR); Belinda Perez Bibbins, Rueil-Malmaison (FR); Nicolas Lopes Ferreira, Rueil-Malmaison (FR); Vincent Coupard, Rueil-Malmaison (FR); Angelique Bisson, Rueil-Malmaison (FR); Jean-Christophe Gabelle, Rueil-Malmaison (FR)

(73) Assignee: IFP Energies Nouvelles, Rueil-Malmaison (FR)

(*) Notice: Subject to any disclaimer, the term of this patent is extended or adjusted under 35 U.S.C. 154(b) by 0 days.

(21) Appl. No.: 17/280,257

(22) PCT Filed: Sep. 26, 2019

(86) PCT No.: PCT/EP2019/075973
§ 371 (c)(1),
(2) Date: Mar. 26, 2021

(87) PCT Pub. No.: WO2020/064901
PCT Pub. Date: Apr. 2, 2020

(65) Prior Publication Data
US 2022/0041972 A1 Feb. 10, 2022

(30) Foreign Application Priority Data
Sep. 28, 2018 (FR) ........................ 1871105

(51) Int. Cl.
*B08B 3/08* (2006.01)
*C12M 1/00* (2006.01)
(Continued)

(52) U.S. Cl.
CPC ............... *C12M 39/00* (2013.01); *B08B 3/08* (2013.01); *B08B 7/02* (2013.01); *B08B 7/04* (2013.01)

(58) Field of Classification Search
CPC . C12M 39/00; B08B 3/08; B08B 7/02; B08B 7/04
See application file for complete search history.

(56) References Cited

U.S. PATENT DOCUMENTS

| 4,524,139 A | 6/1985 | Fuchs |
| 10,494,597 B2 | 12/2019 | Bernfeld et al. |
| 2017/0253846 A1 | 9/2017 | Bernfeld et al. |

FOREIGN PATENT DOCUMENTS

WO 2015/157607 A1 10/2015

OTHER PUBLICATIONS

Shamsudin et al. Production of Acetone, Butanol and Ethanol (ABE) by Clostridium saccharoperbutylacetonicum N1-4 with Different Immobilization System Journal of Biological Sciences 9(10): 1923-1928 (Year: 2006).*

(Continued)

Primary Examiner — Erin F Bergner
(74) Attorney, Agent, or Firm — Millen White Zelano and Branigan, PC; Csaba Henter (57) ABSTRACT

The present invention relates to a process for cleaning a solid support of a fermentation reactor for the production of alcohols by fermentation using a sugary fluid, the solid support comprising a polyurethane foam inoculated with a biomass produced by a solvent-producing strain belonging to the genus *Clostridium*, the process comprising placing the (Continued)

solid support in contact with a fluid originating from the fermentation must enriched in alcohol and/or acetone and/or an aqueous solution at basic pH.

17 Claims, 2 Drawing Sheets

(51) Int. Cl.
    *B08B 7/02*         (2006.01)
    *B08B 7/04*         (2006.01)

(56)           References Cited

OTHER PUBLICATIONS

International Search Report dated Nov. 6, 2019 issued in corresponding PCT/EP2019/075973 application (2 pages).

* cited by examiner

METHOD FOR CLEANING A SOLID SUPPORT OF A FERMENTATION REACTOR COMPRISING A CONTAMINATED POLYURETHANE FOAM

TECHNICAL FIELD

The present invention relates to a process for cleaning a solid support of a fermentation reactor for the production of alcohols by fermentation using a fluid mainly comprising sugar (or sugary fluid), the solid support being inoculated with a solvent-producing strain belonging to the *Clostridium* genus.

PRIOR ART

In order to meet the energy transition challenges, considerable research is being conducted to develop "green" processes, affording access to chemical intermediates as an alternative to the refining of petroleum and/or petrochemistry.

Alcohols derived from fermentation processes (e.g. isopropanol and n-butanol) are among the most promising replacements for petrochemical derivatives. ABE (Acetone—Butanol—Ethanol) fermentation, performed by microorganisms belonging to the genus *Clostridium*, is one of the oldest fermentations to have been industrialized (at the start of the 20th century) and has since been extensively studied (Sauer M., 2016, FEMS Microbiol. Lett., Vol. 363, No. 13). More recently, the development of genetic tools dedicated to these strains has made it possible to modify them to make them produce other chemical molecules of interest. One of the examples is the integration by genetic engineering of a genetic structure for converting acetone into isopropanol (Collas et al., 2012, Appl. Microbiol. Biotechnol. Exp., Vol. 2, No. 45) and the production in fine of an Isopropanol/Butanol/Ethanol (IBE) mixture from a strain initially capable of making ABE (Collas et al.; Dai et al., 2012, Biotechnol. Biofuels., Vol. 5, No. 44; Lee et al., 2012, Appl. Environ. Microbiol., Vol. 78, pages 1416-1423).

As regards the fermentation approach employed in this type of process, production in "batch" mode remains the conventional method for ABE or IBE fermentations. Many other processes, including fed-batch and continuous processes with cells in homogeneous suspension in a reactor, may also be envisioned.

In the case of ABE or IBE fermentation, the presence of n-butanol even at very low concentrations in the medium (<10 g/L) is a major curb on the growth of these microorganisms (Qureshi & Blaschek, 2001, J. Ind. Microbiol. Biotechnol., Vol. 27, pages 287-291). This is a major technical problem when it is desired to perform an industrial production of these alcohols by fermentation, the presence of n-butanol limiting the concentration of the cells in the fermentation medium and thus the performance of the process. This cell concentration is mainly controlled by the dilution rate applied in the process. Said rate therefore cannot be too high, to avoid cell "wash-out" in the fermenter; it also cannot be too low, to avoid excessive accumulation of butanol or to avoid causing clogging problems by decantation of the microorganisms. For these reasons, strong interest has been shown in recent years in methods directed toward increasing microbial biomass notably via processes of cell retention (Mariano et al., 2016, chapter 4, taken from "Commercializing biobased product", Royal Society of Chemistry) or of extraction during the fermentation of the alcohols produced and mainly of n-butanol (Pablo Jimenez-Bonilla & Yi Wang, 2018, in situ biobutanol recovery from clostridial fermentations: a critical review, Critical Reviews in Biotechnology, 38:3, pages 469-482).

The industrial processes for cleaning fermentation tanks are moreover well known. There are many dedicated manuals in the literature, such as "Les bioréacteurs: risques et prévention [Bioreactors: risks and prevention]", INRS, ED6258, October 2016; and "The Alcohol Textbook", 5th Edition, Nottingham University Press, 2009 from D. R. Kelsall, G. D. Austin and C. Kluhspies. Patent U.S. Pat. No. 4,524,139 describes, for example, a process for regenerating porous materials used in reactors.

However, none of the cited documents proposes means for maintaining the performance of the production processes, notably in the context of fermentation processes using supports enabling cell retention. It is, specifically, necessary to clean these supports when they are worn out, clogged and/or saturated with *Clostridium* biomass. Saturation with bacterial biomass, composed essentially of organic matter (extracellular DNA, polysaccharides, proteins, and active or inactive cells), is one of the main causes of losses of performance in alcohol production processes involving a solid cell retention system. Solutions should thus be found for treating these solid supports in order to regain satisfactory performance levels.

SUMMARY OF THE INVENTION

A first object of the present description is to provide a process for cleaning a solid support of a fermentation reactor for the purpose of reusing it and enabling maintenance of the performance notably in terms of alcohol productivity.

According to a first aspect, the abovementioned object, and other advantages, are achieved by a process for cleaning a solid support of a fermentation reactor for the production of alcohols by fermentation using a sugary fluid. The solid support is characterized by a polyurethane foam inoculated with a solvent-producing strain belonging to the genus *Clostridium* and the process comprises the following cleaning step: placing the solid support in contact with a fluid originating from the fermentation must enriched in alcohol and/or acetone and/or an aqueous solution at basic pH.

According to one or more embodiments, the fluid originating from the fermentation must comprises at least one compound chosen from butanol, isopropanol and ethanol.

According to one or more embodiments, the fluid originating from the fermentation must comprises butanol.

According to one or more embodiments, the fluid originating from the fermentation must comprises at least 10 g/L of the compound.

According to one or more embodiments, the fluid originating from the fermentation must comprises at least one of the following elements: a source of butanol, a beer-column head effluent, a beer-column reflux, a beer-column distillate, an isopropanol-ethanol-water column head mixture, a source of isopropanol, an isopropanol-ethanol-water column tail effluent, and a source of acetone.

According to one or more embodiments, the source of butanol comprises at least 90% by weight of butanol.

According to one or more embodiments, the beer-column head effluent comprises at least 7% by weight of isopropanol and/or at least 10% by weight of butanol.

According to one or more embodiments, the beer-column reflux comprises at least 70% by weight of water and/or at least 5% by weight of isopropanol and/or at least 5% by weight of butanol and/or at least 0.1% by weight of ethanol.

According to one or more embodiments, the beer-column distillate comprises not more than 30% by weight of water and/or at least 10% by weight of isopropanol and/or at least 15% by weight of butanol and/or at least 0.1% by weight of ethanol.

According to one or more embodiments, the IEW column head mixture comprises not more than 15% by weight of water and/or at least 75% by weight of isopropanol and/or at least 0.05% by weight of ethanol.

According to one or more embodiments, the source of isopropanol comprises at least 99% by weight of isopropanol.

According to one or more embodiments, the IEW column tail effluent comprises not more than 40% by weight of water and/or at least 40% by weight of butanol and/or at least 0.05% by weight of ethanol.

According to one or more embodiments, the fluid originating from the fermentation must is enriched with sodium hydroxide.

According to one or more embodiments, the aqueous solution at basic pH is a sodic solution comprising at least 0.5% by weight of sodium hydroxide.

According to one or more embodiments, the polyurethane foam is pressed by a repeated mechanical compression action, during the placing in contact.

Embodiments of the process referenced above and also other features and advantages of said process will emerge on reading the description that follows, which is given purely for nonlimiting illustrative purposes, and with reference to the following drawings.

DESCRIPTION OF THE EMBODIMENTS

Embodiments of the process according to the first aspect will now be described in detail. In the following detailed description, many specific details are presented in order to provide a more in-depth comprehension of the process. However, it will be apparent to a person skilled in the art that the process can be performed without these specific details. In other cases, well-known features have not been described in detail in order to avoid unnecessarily complicating the description.

In that which follows, the term "comprise" is synonymous with (means the same thing as) "include" and "contain", and is inclusive or open and does not exclude other unspecified elements. It is understood that the term "comprise" includes the exclusive and closed term "consist". In addition, in the present description, the terms "approximately", "substantially", "essentially" and "about" are synonymous with (mean the same thing as) a margin of greater and/or less than 10%, preferably 5%, of the given value.

The present description relates to a process for cleaning a solid support of a fermentation reactor for the production of alcohols by fermentation using a sugary fluid, the solid support being inoculated with a biomass produced by a solvent-producing strain (e.g. a strain that is capable of producing, from sugar and/or acids, an alcohol mixture comprising isopropanol, butanol, ethanol and/or acetone) belonging to the genus *Clostridium*.

The Solid Support

The solid support comprises a polyurethane foam. Polyurethane foam is particularly advantageous since it allows not only the production of mixtures of IBEA (Isopropanol—Butanol—Ethanol—Acetone) type, but also allows production of continuous type by immobilization of the bacterial biomass. Specifically, the Applicant has demonstrated that polyurethane foam is capable of fixing bacteria of the genus *Clostridium* in a sufficiently substantial manner (i.e. beyond the dilution rate causing cell washing) making it possible to continuously produce mixtures of IBEA type. Furthermore, polyurethane foam is suitable for immobilization by immersion in a reactor.

According to one or more embodiments, the polyurethane foam comprises at least one of the following features:
  volume cavities (i.e. pores or cells) whose equivalent sphere diameter is between 0.1 and 5 mm, preferably between 0.25 mm and 1.1 mm, preferably between 0.55 and 0.99 mm, and
  an apparent density (i.e. apparent mass per unit volume) measured in air of between 10 and 90 g/L, preferably between 10 and 80 g/L, preferably between 15 and 45 g/L, such as between 20 and 45 g/L or between 25 and 45 g/L.

Description of the Method for Measuring the Pore Diameter: X-Ray Tomography

The equivalent sphere diameter of the volume cavities may notably be obtained by analysis with an X-ray microscanner (e.g. HR 70 kV 200 microA Point focal medium tube; Varian pixel detector: 6 microns; acquisition time: 2 hours) of a sample (e.g. 7 mm×7 mm×15 mm) and reconstruction of a representative volume of the foam (e.g. reconstructed volume 5 mm×5 mm×5 mm with a voxel size of 6 microns), assuming spherical cells.

The diameter measurements were made by 3D image analysis with the Avizo software from 3D volumes acquired with an X-ray microscanner. The cells were artificially closed by image analysis so as to estimate the volume and then the diameter thereof. The diameter of a given cell is likened to that of a sphere of the same volume. The various steps of the image analysis are as follows:
  thresholding of the images (black=cells and white=walls);
  2D partitioning of the "cells" by the xy catchment basin method on Avizo;
  3D partitioning of the "cells" by the 3D catchment basin method on Avizo;
  removal of the edge cells (incomplete cells);
  measurement of the volumes of the reconstructed cells;
  estimation of the cell diameters (diameters of equivalent spheres of the same volume); and
  size distribution of the cells for comparison.

The Biomass Produced by the Strain Belonging to the Genus *Clostridium*

The bacterial biomass is mainly adsorbed in the form of a biofilm onto the solid support. According to one or more embodiments, the biomass is produced by a microorganism belonging to the genus *Clostridium* and capable of producing mixtures of IBEA type (e.g. *Clostridium acetobutylicum*, *Clostridium beijerinckii*, *Clostridium saccharobutylicum*, *Clostridium tyrobutyricum*, *C. saccharoperbutylacetonicum*, *C. butylicum* and other *Clostridium* sp). Preferably, the bacteria are strains belonging to the species *Clostridium beijerinckii* and/or *Clostridium acetobutylicum*. The bacteria used in the process may or may not be genetically modified strains. They may be derived from strains which naturally produce isopropanol and/or from *Clostridium* strains which naturally produce acetone and which are genetically modified to make them produce isopropanol. More globally, the majority of the "solvent-producing" *Clostridium* species may be used.

Immersion and Use of the Solid Support for Fermentation

According to one or more embodiments, the solid support is partially or totally immersed in the fermentation reactor, in order notably to increase the formation of biofilms and to improve the performance. According to one or more embodiments, the solid support forms a fluidized bed or a fixed bed in the fermentation reactor. According to one or more embodiments, the solid support is in the form of one or more blocks. According to one or more embodiments, the solid support is in the form of a net or of a latticed container comprising a plurality of polyurethane foam cubes, parallelepipeds or any other three-dimensional shapes (chips), for example of which at least one dimension is at least 3 mm.

Fermentation Process

Figure 1:
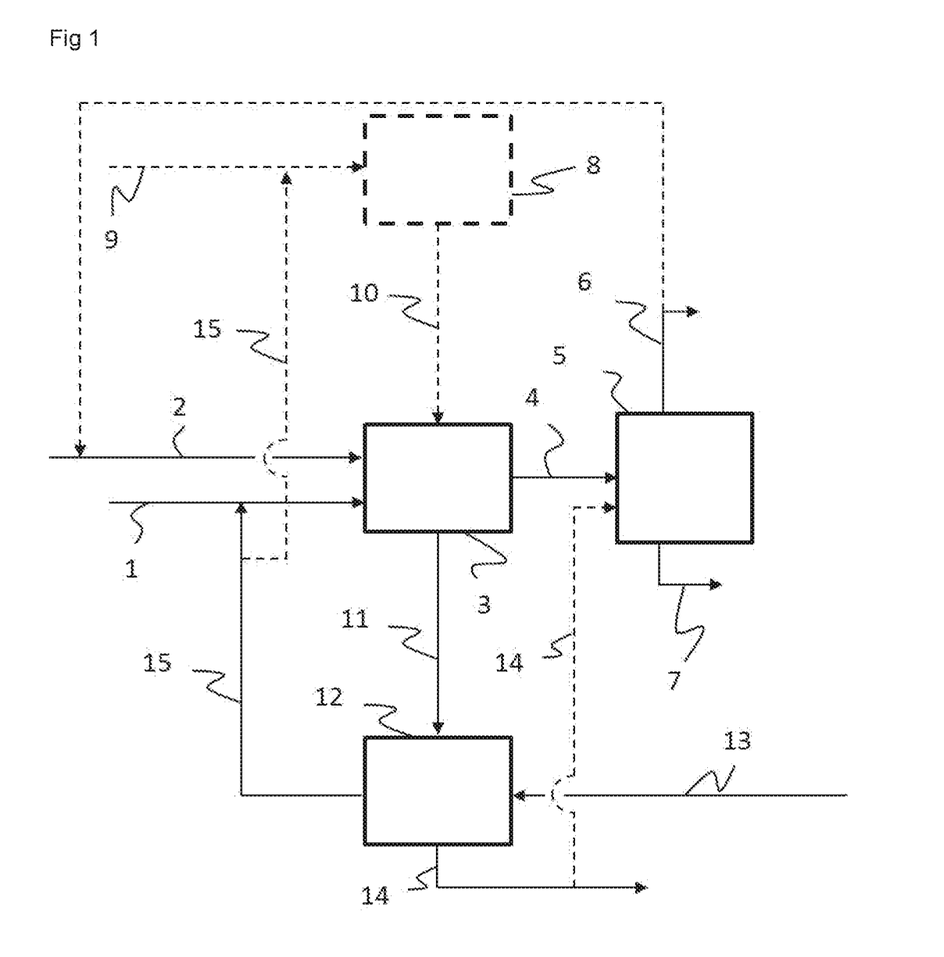
FIG. 1 is a schematic view of an alcohol production process also comprising a process for cleaning a solid support according to embodiments of the present description.

FIG. 1 shows a scheme for producing an alcohol mixture from a substrate of lignocellulosic biomass type.

With reference to FIG. 1, the solid support is introduced, for example via line 1 (or via any other means), and a sugary fluid 2 comprising, for example, C5 and/or C6 sugars is introduced into the fermentation reactor 3 to undergo a fermentation step. A sugary fluid corresponds to a fluid comprising (mainly) sugars. The sugary fluid may comprise, for example, an aqueous solution of C5 and/or C6 sugars obtained from lignocellulose, and/or of sugars obtained from sugar-producing plants (e.g. glucose, fructose and sucrose), and/or of sugars obtained from starchy plants (e.g. dextrins, maltose and other oligomers, or even starch).

In the fermentation reactor 3, the sugary fluid is placed in contact with the bacterial biomass supported by the solid support. The fermentable sugars (e.g. C5 and/or C6 sugars) are thus transformed into alcohols and/or solvents by the microorganisms to produce a fermentation must (or liquor or wine), which is notably enriched in isopropanol, butanol, ethanol and acetone relative to the sugary fluid.

According to one or more embodiments, the fermentation step in the fermentation reactor 3 is performed at a temperature of between 20° C. and 40° C., preferably between 30° C. and 37° C., so that the fermentation must removed via a line 4 comprises fermentation reaction products of IBEA type.

The fermentation must is introduced via line 4 into a separation unit 5 for separating and extracting the water (recyclable) and the compounds of interest from the fermentation must (e.g. IBEA compounds), said compounds being removed, for example, via at least one line 6. The separation residues, commonly known as vinasses, are removed from the separation unit 5, for example via line 7. The vinasses are generally composed of water and also of any liquid or solid product not converted or extracted during the preceding steps. The separation unit 5 may implement one or more distillations, and optionally a separation of the solid matter, optionally in suspension, for example by centrifugation, decantation and/or filtration optionally followed by a system for drying the extracted solids. The water separated from the solids may also be recycled into the process, after optional purification (water treatment).

Several fermentation reactor 3 implementations or technologies existing in the prior art are suitable for immobilizing the bacterial biomass by adsorption on the solid support, and can do so whether the implementation takes place inside the fermentation reactor 3 or in a secondary tank in "in-stream" mode. For example, the bacterial biomass may be immobilized indirectly in a secondary tank 8 (optional) fed, for example via line 9 (or via any other means), with solid support, the secondary tank 8 functioning, for example, in "in-stream" mode relative to the fermentation reactor 3. The solid support thus loaded with bacterial biomass in the secondary tank 8 may then be introduced into the fermentation reactor 3, for example via line 10 (or via any other means).

Fermentation must Separation Process

Figure 2:
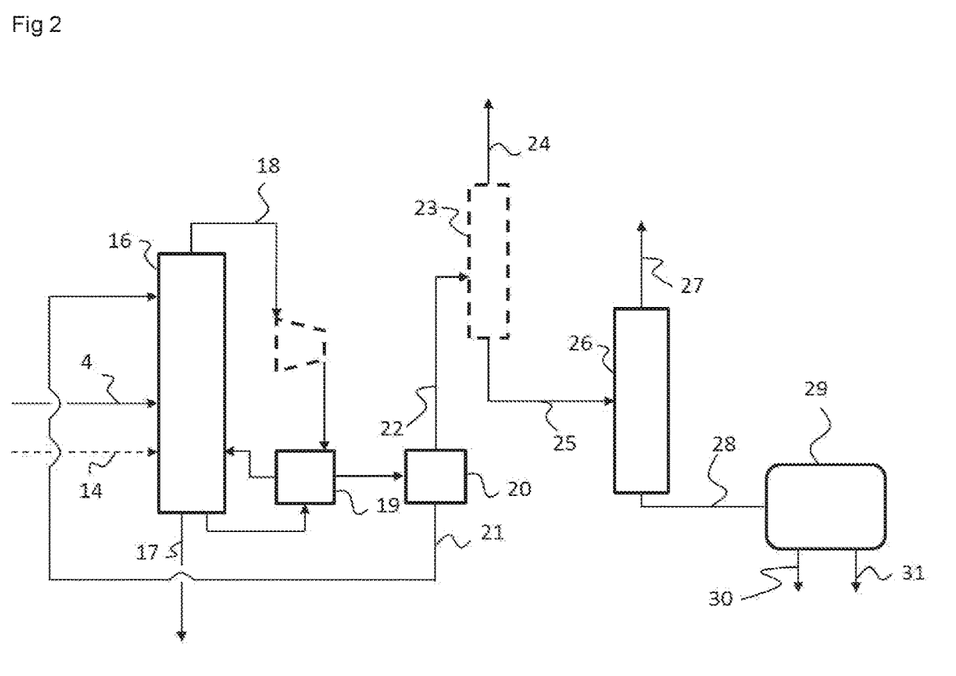
FIG. 2 is a schematic view of the separation unit used in the process of FIG. 1.

FIG. 2 shows a schematic diagram of a unit 5 for separating out the alcohols produced by a fermentation of IBE type, i.e. an Isopropanol-Butanol-Ethanol mixture optionally with acetone.

In accordance with a preferred embodiment of the process for producing fermentation products according to the invention, the fermentation must 4 is sent into a first distillation column 16, also known as the "beer column". The beer column 16 is designed to separate out a portion of the water 17 contained in the mixture, which is recovered at the bottom of the beer column 16. The composition of this water is such that it may at least partly (e.g. at least 50% by weight) be recycled (e.g. directly) upstream of the fermentation reactor 3. The beer-column head effluent 18 is an aqueous mixture enriched in IBEA.

According to one or more embodiments, as shown in FIG. 2, the beer column 16 uses a reboiling system 19, preferably by mechanical recompression of the vapors of the beer-column head effluent 18. These vapors (recompressed) condense by means of a reboiler (heat exchanger) of the column, thus enabling the vaporization of the liquid 18 at the bottom of the beer column. This optional system makes it possible to lower the energy demand of the beer column 16 by about 30% to 50%.

According to one or more embodiments, the beer-column head effluent 18 is partly recycled into the beer column 16 as a reflux known as the "beer-column reflux" 21. The other part of the head effluent not recycled from the beer column 16, also known as the "beer-column distillate" 22, is sent into an optional second distillation column 23, also known as an "acetone column". According to one or more embodiments, the beer column 16 is implemented with a decantation vessel 20 placed downstream of the beer column 16 and upstream of the second distillation column 23 to separate the beer-column distillate 22 from the beer-column reflux 21.

The role of the acetone column 23 is to separate the acetone from the alcohol stream, the acetone being extracted as the head effluent 24 from the acetone column 23, and to produce an aqueous mixture concentrated in isopropanol-butanol-ethanol 25 which is withdrawn at the bottom of the acetone column 23.

The aqueous mixture concentrated in IBE 25 is then sent into a third distillation column 26, also known as the "isopropanol-ethanol-water column" or "IEW" column, designed and operated to separate a head mixture 27 containing ethanol/isopropanol/water of azeotropic composition (+acetone and other uncondensable matter ($CO_2$, $H_2$, $N_2$ and traces of other organic or inorganic compounds, when the acetone column 23 is not present; in this case, the IEW column preferably comprises a zone known as the head pasteurization zone for separating out an IEW cut free of uncondensable matter) and a tail effluent 28 concentrated in butanol. According to one or more embodiments, in order to control the demixing which may occur at and above a certain concentration of butanol, the IEW column 26 is equipped with one or more liquid/liquid/vapor demixing zones. According to one or more embodiments, the IEW column 26 may be operated at a higher pressure (e.g. between 0.3 and 0.7 MPa at the column head) so as to eliminate this demixing.

According to one or more embodiments, the IEW column head mixture 27 may be directed toward additional separation equipment (not shown) to produce a fraction enriched in isopropanol. In this case, the IEW column head mixture 27 may be dried, for example by molecular sieves located in the reflux loop of the IEW column 26 or after the IEW column 26, so as to produce an anhydrous cut. This anhydrous cut may subsequently be separated into pure alcohols, ethanol at the head and isopropanol at the bottom of the additional separation equipment.

If it is necessary to dry and separate a butanol cut from the IEW column tail effluent 28, this may be treated by a heteroazeotropic distillation system 29 to separate an effluent enriched in butanol 30 and an effluent enriched in water 31.

Process for Cleaning the Solid Support

When the performance of the alcohol production process begins to decline (e.g. nominal performance: alcohol productivity greater than or equal to 2 g/L/h), notably when the productivity becomes less than 60% of the nominal performance (e.g. between 1000 and 2000 hours of functioning of the production process), it is possible to perform a step of cleaning the solid support of the fermentation reactor 3 using a cleaning fluid chosen from a fluid originating from the fermentation must and an aqueous solution at basic pH.

In effect, although the bacterial biomass load may be very high at the end of production (for example: load of 150 g of biomass per liter of polyurethane foam measured at the end of a test lasting 750 hours), it has been found that a fluid originating from the fermentation must enriched in alcohol and/or acetone and/or an aqueous solution at basic pH makes it possible to eliminate the majority of the biomass immobilized in the polyurethane foam. Specifically, the cleaning process according to the first aspect makes it possible to remove the bacterial biomass immobilized on the solid support, notably with a removal of 97-99% by weight relative to the total weight of the bacterial biomass. The solid support thus cleaned is thus essentially entirely freed of the bacterial load. Furthermore, the solid support is not torn (mechanical strength) and appears in perfect conformity with the new solid support. Another advantage, but not the least, is that the polyurethane foam thus cleaned (e.g. clean and optionally sterile) may be reused in the process with maintenance of the performance of the fermentation reactor 3.

According to one or more embodiments, the fluid originating from the fermentation must comprises at least one compound chosen from butanol, isopropanol and ethanol. According to one or more embodiments, the fluid originating from the fermentation must comprises butanol. According to one or more embodiments, the fluid originating from the fermentation must comprises at least 10 g/L of the compound, preferably at least 15 g/L, preferably at least 17 g/L. Butanol, and to a lesser extent isopropanol and ethanol, for example at concentrations greater than tens of grams per liter, are notably toxic to microorganisms belonging to the genus *Clostridium*. These alcohols are notably capable of penetrating the cell membranes and blocking the cellular activity.

According to one or more embodiments, the fluid originating from the fermentation must comprises (or consists of) at least one of the following elements:
- a source of butanol, such as the butanol-enriched effluent 30 or an external source of butanol,
- the beer-column head effluent 18,
- the beer-column reflux 21,
- the beer-column distillate 22,
- the IEW column head mixture 27,
- a source of isopropanol, such as the isopropanol-enriched fraction of the IEW column head mixture 27 or an external source of isopropanol,
- the IEW column tail effluent 28, and
- a source of acetone, such as the acetone-column head effluent 24 or an external source of acetone.

According to one or more embodiments, the source of butanol comprises at least 90% by weight of butanol, preferably at least 99% by weight of butanol, very preferably at least 99.5% by weight of butanol (e.g. with not more than 0.4% by weight of water). Traces of other alcohols (ethanol, isopropanol, other monofunctional aliphatic alcohols containing 5 or 6 carbons, acids corresponding to these alcohols) may also be present at less than 0.5% by weight, preferentially at less than 0.1% by weight. According to one or more embodiments, the source of butanol has a temperature of at least 50° C., preferably a temperature of at least 70° C., very preferably a temperature of at least 100° C.

According to one or more embodiments, the beer-column head effluent 18 comprises at least 7% by weight of isopropanol and/or at least 10% by weight of butanol, preferably at least 10% by weight of isopropanol and/or at least 15% by weight of butanol, such as comprising 67% by weight of water, 13% by weight of isopropanol, 18% by weight of butanol and 0.4% by weight of ethanol+traces of acetone and butyric acid. According to one or more embodiments, uncondensable matter (e.g. $CO_2$, $H_2$, $N_2$) is also present in the beer-column head effluent 18. According to one or more embodiments, the beer-column head effluent 18 comprises less than 10% by weight of uncondensable matter, preferably less than 5% by weight, for example between 2% and 3% by weight, preferably less than 1% by weight. According to one or more embodiments, the beer-column head effluent 18 has a temperature of at least 100° C. and/or a pressure of at least 0.1 MPa abs, preferably a temperature of at least 108° C. and/or a pressure of at least 0.15 MPa abs, very preferably a temperature of at least 122.7° C. (for example between 130 and 150° C.) and/or a pressure of at least 0.321 MPa abs (recompressed head vapor).

According to one or more embodiments, the beer-column reflux 21 comprises at least 70% by weight of water and/or at least 5% by weight of isopropanol and/or at least 5% by weight of butanol and/or at least 0.1% by weight of ethanol and optionally traces of acetone and/or of butyric acid, preferably from 7% by weight to 15% by weight of isopropanol and/or from 7% by weight to 20% by weight of butanol and/or from 0.2% by weight to 2% by weight of ethanol, preferably from 9% by weight to 13% by weight of isopropanol and/or from 8% by weight to 15% by weight of butanol and/or from 0.2% by weight to 0.5% by weight of ethanol, such as 80% by weight of water, 10% by weight of isopropanol, 9% by weight of butanol, 0.5% by weight of ethanol and traces of acetone and butyric acid. According to one or more embodiments, the beer-column reflux 21 has a temperature of at least 20° C. and/or a pressure of at least 0.1 MPa abs, preferably a temperature of at least 30° C. and/or a pressure of at least 0.11 MPa abs, very preferably a temperature of at least 35° C. and/or a pressure of at least 0.13 MPa abs.

According to one or more embodiments, the beer-column distillate 22 comprises not more than 30% by weight of water and/or at least 10% by weight of isopropanol and/or at least 15% by weight of butanol and/or at least 0.1% by weight of ethanol and optionally traces of acetone and/or of butyric acid, preferably at least 15% by weight of isopropanol and/or at least 25% by weight of butanol and/or at least 0.15% by weight of ethanol, preferably at least 20% by weight of isopropanol and/or at least 35% by weight of butanol and/or at least 0.2% by weight of ethanol, such as 28% by weight of water, 22% by weight of isopropanol, 48% by weight of butanol, 0.5% by weight of ethanol and traces of acetone and butyric acid. According to one or more embodiments, the beer-column distillate 22 has a temperature of at least 20° C. and/or a pressure of at least 0.1 MPa abs, preferably a temperature of at least 30° C. and/or a pressure of at least 0.12 MPa abs, very preferably a temperature of at least 35° C. and/or a pressure of at least 0.13 MPa abs.

According to one or more embodiments, the IEW column head mixture 27 comprises not more than 15% by weight of water and/or at least 75% by weight of isopropanol and/or at least 0.05% by weight of ethanol and optionally traces of acetone and/or of butanol and/or of butyric acid, preferably at least 80% by weight of isopropanol and/or at least 0.075% by weight of ethanol, preferably at least 82% by weight of isopropanol and/or at least 0.1% by weight of ethanol, such as 12% by weight of water, 85% by weight of isopropanol, 2% by weight of ethanol and traces of acetone, butanol and butyric acid. According to one or more embodiments, the IEW column head mixture 27 has a temperature of at least 20° C. and/or a pressure of at least 0.1 MPa abs, preferably a temperature of at least 30° C. and/or a pressure of at least 0.11 MPa abs, very preferably a temperature of at least 35° C. and/or a pressure of at least 0.13 MPa abs.

According to one or more embodiments, the source of isopropanol comprises at least 99% by weight of isopropanol, very preferably at least 99.5% by weight of isopropanol (e.g. with not more than 0.5% by weight of water).

According to one or more embodiments, the IEW column tail effluent 28 comprises not more than 40% by weight of water and/or at least 40% by weight of butanol and/or at least 0.05% by weight of ethanol and optionally traces of acetone and/or of isopropanol and/or of butyric acid, preferably at least 50% by weight of butanol, preferably at least 60% by weight of butanol, such as 35% by weight of water, 65% by weight of butanol, 2% by weight of ethanol and traces of acetone, isopropanol and butyric acid. According to one or more embodiments, the IEW column tail effluent 28 has a temperature of at least 20° C. and/or a pressure of at least 0.1 MPa abs, preferably a temperature of at least 30° C. and/or a pressure of at least 0.11 MPa abs, very preferably a temperature of at least 35° C. and/or a pressure of at least 0.12 MPa abs.

According to one or more embodiments, the fluid originating from the fermentation must comprises sodium hydroxide, for instance at least 0.5% by weight of sodium hydroxide, preferably at least 1% by weight of sodium hydroxide (e.g. 2% by weight of sodium hydroxide).

According to one or more embodiments, the aqueous solution at basic pH is an external solution. According to one or more embodiments, the aqueous solution at basic pH is a sodic solution comprising at least 0.5% by weight of sodium hydroxide, preferably at least 1% by weight of sodium hydroxide (e.g. 2% by weight of sodium hydroxide).

According to one or more embodiments, the cleaning fluid is placed in contact with the solid support counter-currentwise relative to the direction of flow of the sugary fluid or fermentation must in the fermentation reactor 3. According to one or more embodiments, the cleaning fluid is placed in contact with the solid support co-currentwise relative to the direction of flow of the sugary fluid or fermentation must in the fermentation reactor 3.

According to one or more embodiments, the polyurethane foam is pressed by a repeated mechanical compression action, before, preferably during, and/or after the step of cleaning the solid support with the cleaning fluid. It has notably been found that the polyurethane foam is not torn during the pressing (mechanical strength) and appears perfectly in conformity with the native foam.

According to one or more embodiments, the solid support is cleaned in the fermentation reactor 3 itself. According to one or more embodiments, the cleaning process comprises the stoppage of the alcohol production in the fermentation reactor 3 during the cleaning step. According to one or more embodiments, the step of cleaning a first fermentation reactor is performed in parallel with a step of producing alcohol in a second fermentation reactor ("swing" type continuous mode).

According to one or more embodiments, as shown in FIG. 1, the cleaning process comprises the removal of the solid support from the fermentation reactor 3, for example via line 11 (or via any other means), to clean said solid support outside the vat, for example by placing the solid support in contact with a stream 13 of cleaning fluid in a dedicated tank 12.

According to one or more embodiments, a soiled cleaning fluid 14 is extracted from the dedicated tank at 12 and the cleaned solid support is reintroduced into the fermentation reactor 3 (or the optional secondary tank 8), for example via line 15 (or via any other means).

According to one or more embodiments, the entire solid support present in the fermentation reactor 3 is extracted in a single stage. According to one or more embodiments, the solid support present in the fermenter is extracted in several stages, for example when the solid support forms a fluidized bed (e.g. mobile bed of polyurethane foam). In either case, it is not necessary to stop the production or to envisage a "swing" mode since the solid support to be cleaned can be withdrawn and replaced permanently with cleaned and/or new solid support.

According to one or more embodiments, the circulation of the solid support in the fermentation reactor 3 takes place from the bottom upward (natural tendency to float).

According to one or more embodiments, the circulation of the solid support in the fermentation reactor 3 takes place counter-currentwise relative to the introduction of the sugary fluid into the fermentation reactor 3.

According to one or more embodiments, the removal and addition of the solid support in the fermentation reactor 3 is performed continuously or in programmed sequences. According to one or more embodiments, at least one portion of new solid support is introduced continuously or in programmed sequences into the fermentation reactor 3 (or the optional secondary tank) with a portion of cleaned solid support.

According to one or more embodiments, the state of cleanliness of the solid support is controlled by scanning electron microscopy and/or by X-ray tomography. For example, a worn out polyurethane foam appears covered with biological matter (dead or live bacteria and polymers), whereas on clean polyurethane foam, the porous structure is apparent. According to one or more embodiments, the cleaning step is stopped when the proportion of clogged pores of the polyurethane foam is less than 10%.

According to one or more embodiments, after the step of cleaning with the fluid originating from the fermentation must, said soiled cleaning fluid 14 is recycled into the beer column 16. According to one or more embodiments, the soiled cleaning fluid 14 is recycled toward a feed plate chosen so as not to disrupt the functioning of the beer column 16, for example below the bottom liquid level of the column, or else into the feed liquid of the reboiler. According to one or more embodiments, the solid waste included in the soiled cleaning fluid 14 falls and is removed at the bottom of the beer column 16, as is performed in ethanol distilleries, for example.

According to one or more embodiments, the cleaning process also comprises a step of washing the solid support with water before or after the cleaning step, optionally with a repeated mechanical compression action, for example using two volumes of water per one volume of solid support. According to one or more embodiments, the washing step is performed at a temperature of at least 60° C., very preferably a temperature of at least 80° C.

The following chemical agents may be used during the washing step: weak bases, chelating agents, surfactants, acids, bleaching agents. Depending on the desired degree of cleanliness of the solid support, in a non-exhaustive manner, the following chemical agents may be used during the washing step in order to sanitize the solid support: sodium hypochlorite, chlorine dioxide, iodide, peracetic acid, quaternary ammonium compounds. For a cleaning step with a disinfecting effect, the following chemical agents may be used: alkylmercury derivatives, β-propiolactone. For a cleaning step with a sterilizing effect, use may be made of steam, superheated steam, or heating using heating resistances or heat exchangers, or a UHT (ultra-high-temperature) process. According to one or more embodiments, the washing step is performed with steam at a temperature of at least 121° C., for example for 20 to 30 minutes. According to one or more embodiments, the washing step is performed with superheated steam at a temperature of between 120 and 140° C., for example for a predetermined time. According to one or more embodiments, the washing step is performed via a UHT process at a temperature of between 140 and 150° C., for example for 2 to 5 seconds (e.g. at a pressure of less than or equal to 0.2 MPa). According to one or more embodiments, the solid support is sterilized after the cleaning step, for example when the cleaning is performed in the fermentation reactor 3. The sterilization step is notably optional when the cleaning fluid comprises hot butanol (e.g. 50° C.).

According to one or more embodiments, a step of rinsing the solid support with cold water or water at ambient temperature (e.g. 3-30° C.) is performed, preferably until the alkalinity is removed, for example with monitoring of the pH (e.g. pH paper). According to one or more embodiments, the solid support may be rinsed directly with water at a temperature equal to the fermentation temperature (energetically easier).

EXAMPLES

Washing with Hot Sodic Solution and Mechanical Action

After 750 hours of functioning of a process for fermentation of a sugary fluid, the fermentation reactor is emptied and the contaminated solid support (i.e. support inoculated with a biomass produced by a solvent-producing strain belonging to the genus *Clostridium*) is extracted. In this example, more than 150 g of biomass per liter of polyurethane foam was measured.

The polyurethane foam is washed with hot water at 60° C. with a repeated mechanical compression action, in 2 volumes of water per 1 volume of polyurethane foam.

The polyurethane foam is then cleaned with a sodic solution (2%) at a temperature of 60° C., with a repeated mechanical compression action, in 2 volumes of water per 1 volume of polyurethane foam.

Finally, the foam is rinsed with hot water, and then with cold water until the alkalinity has been removed, with monitoring using pH paper.

The efficiency of removal of the bacterial biomass is 97-99%. It was determined by measuring the matter in suspension (i.e. "DM" or dry mass in the usual manner, depending on whether a liquid or a wet solid is concerned) at the end of washing. The polyurethane foam is thus virtually entirely freed of the bacterial load. The polyurethane foam is not torn (mechanical strength) and appears perfectly in conformity with the native foam.

The performance of a washed polyurethane foam was measured in a column test and compared with that of polyurethane foam. There was no real difference between the two tests, the washed polyurethane foam having substantially better performance than the virgin polyurethane foam.

Washing with Hot Butanol

Two batches of polyurethane foams were cut into cubes 2×2×3.5 mm in size and used in two fermentation processes. The polyurethane foams thus underwent sterilization, and then colonization with the bacteria during continuous culturing lasting 175 hours.

The polyurethane foams were recovered on conclusion of the fermentation processes and were rinsed three times with distilled water in order to remove the majority of the biofilm and cell residues. The polyurethane foams were then impregnated with a solution containing 50% v/v of n-butanol in distilled water, and were then placed in a water bath for 15 minutes at 70° C. in closed 250 mL glass flasks. The foams were then rinsed again five times with distilled water, and were then oven-dried for 24 hours at 45° C.

The performance of the polyurethane foams before and after washing were measured and compared. The operating conditions applied in the fermentation processes are strictly identical.

The fermentation processes performed with foams washed with butanol show satisfactory performance over 200 hours of continuous culturing. Good launching of the culturing is observed, with a high concentration of cells after 100 hours of culturing. These tests show that the productivity after 175 hours of culturing is satisfactory. The washing and re-use of the foams for a second fermentation cycle therefore does not appear to have an impact on the growth and colonization of the bacteria on the support.

The invention claimed is:

1. A process for cleaning a solid support of a fermentation reactor for the production of alcohols by fermentation of a sugary fluid, the solid support comprising a polyurethane foam inoculated with a bacterial biomass produced by a solvent-producing strain belonging to the genus *Clostridium*, the process comprising placing the solid support in contact with a fluid originating from the fermentation must containing alcohol and/or a fluid originating from the fermentation must containing acetone the fluid originating from the fermentation must eliminates 97-99% by weight of the bacterial biomass immobilized in the polyurethane foam relative to the total weight of the bacterial biomass.

2. The process as claimed in claim 1, in which the fluid originating from the fermentation must comprises at least one compound selected from the group consisting of butanol, isopropanol and ethanol.

3. The process as claimed in claim 2, in which the fluid originating from the fermentation must comprises butanol.

4. The process as claimed in claim 2, in which the fluid originating from the fermentation must comprises at least 10 g/L of the at least one compound.

5. The process as claimed in claim 1, in which the fluid originating from the fermentation must comprises at least one of the following: a source of butanol, a beer-column head effluent, a beer-column reflux, a beer-column distillate, an isopropanol-ethanol-water column head mixture, a source of isopropanol, an isopropanol-ethanol-water column tail effluent, or a source of acetone.

6. The process as claimed in claim 5, in which the source of butanol comprises at least 90% by weight of butanol.

7. The process as claimed in claim 5, in which the beer-column head effluent comprises at least 7% by weight of isopropanol and/or at least 10% by weight of butanol.

8. The process as claimed in claim 5, in which the beer-column reflux comprises at least 70% by weight of water and/or at least 5% by weight of isopropanol and/or at least 5% by weight of butanol and/or at least 0.1% by weight of ethanol.

9. The process as claimed in claim 5, in which the beer-column distillate comprises not more than 30% by weight of water and/or at least 10% by weight of isopropanol and/or at least 15% by weight of butanol and/or at least 0.1% by weight of ethanol.

10. The process as claimed in claim 5, in which the isopropanol-ethanol-water column head mixture comprises not more than 15% by weight of water and/or at least 75% by weight of isopropanol and/or at least 0.05% by weight of ethanol.

11. The process as claimed in claim 5, in which the source of isopropanol comprises at least 99% by weight of isopropanol.

12. The process as claimed in claim 5, in which the isopropanol-ethanol-water column tail effluent comprises not more than 40% by weight of water and/or at least 40% by weight of butanol and/or at least 0.05% by weight of ethanol.

13. The process as claimed in claim 1, in which the fluid originating from the fermentation must contains sodium hydroxide.

14. The process as claimed in claim 1, in which the polyurethane foam is pressed by a repeated mechanical compression action during the placing of the solid support in contact with the fluid originating from the fermentation must.

15. The process as claimed in claim 1, in which the fluid originating from the fermentation must eliminates the majority of the bacterial biomass immobilized in the polyurethane foam.

16. The process as claimed in claim 1, wherein the polyurethane foam has pores that are clogged by bacterial biomass, and the cleaning process results in a proportion of clogged pores being less than 10%.

17. The process as claimed in claim 1, further comprising rinsing the solid support.

\* \* \* \* \*